United States Patent [19]
Furuta et al.

[11] 4,182,571
[45] Jan. 8, 1980

[54] EGG INSPECTING APPARATUS

[75] Inventors: Naofumi Furuta, Kochino; Hisatoshi Saito, Yokohama, both of Japan

[73] Assignee: Kewpie Kabushiki Kaisha, Tokyo, Japan

[21] Appl. No.: 880,174

[22] Filed: Feb. 22, 1978

[51] Int. Cl.$^2$ .................. A01K 43/00; G01N 33/08
[52] U.S. Cl. ........................... 356/53; 356/407
[58] Field of Search .............. 356/53, 320, 407, 419

[56] References Cited
U.S. PATENT DOCUMENTS

| | | | |
|---|---|---|---|
| 3,031,077 | 4/1962 | Mumma et al. | 356/53 |
| 3,770,354 | 11/1973 | Tsuruta et al. | 356/407 |
| 4,039,259 | 8/1977 | Saito et al. | 356/53 |
| 4,063,822 | 12/1977 | de Jong et al. | 356/53 |

*Primary Examiner*—Vincent P. McGraw
*Attorney, Agent, or Firm*—Oblon, Fisher, Spivak, McClelland & Maier

[57] ABSTRACT

An egg inspecting apparatus utilizes the light reception signals of 575 mμ, 590 mμ, and 620 mμ obtained from the light beams passed through an egg to be inspected, in such a manner the light reception signal of 575 mμ is calibrated by basing on the light reception signal 590 mμ and is compared with a blood-containing egg level to select blood-containing eggs, and the light reception signal of 620 mμ is compared with an addled egg level to select addled eggs.

2 Claims, 5 Drawing Figures

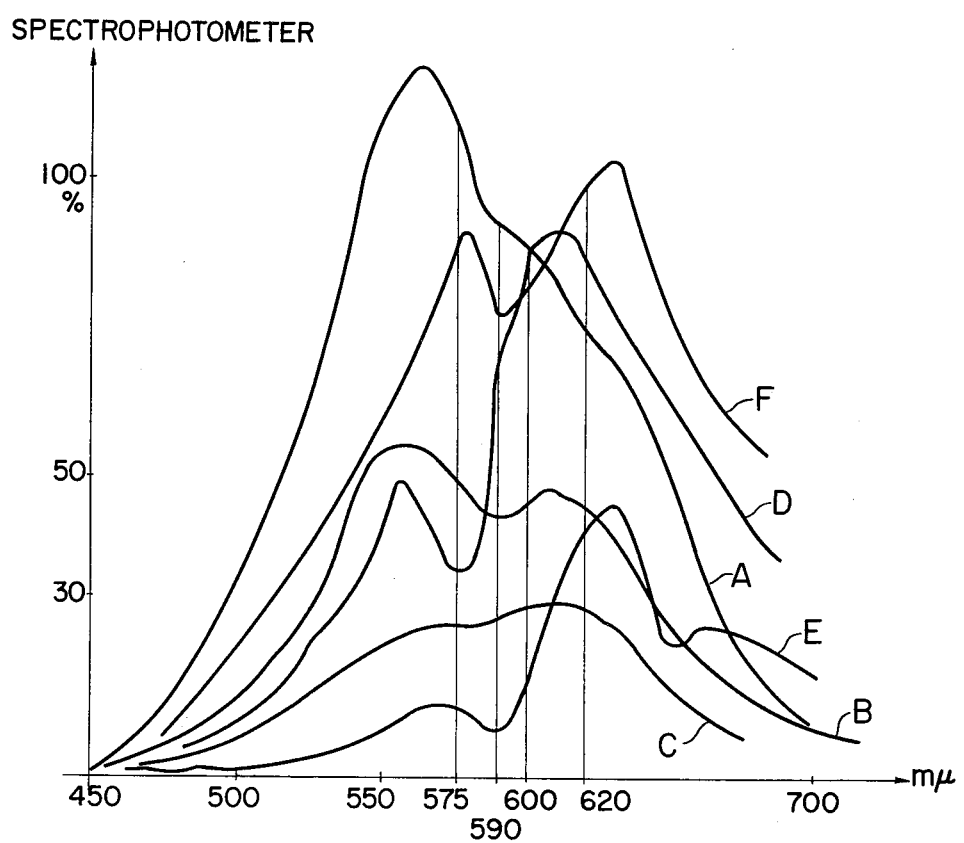
F I G. 1

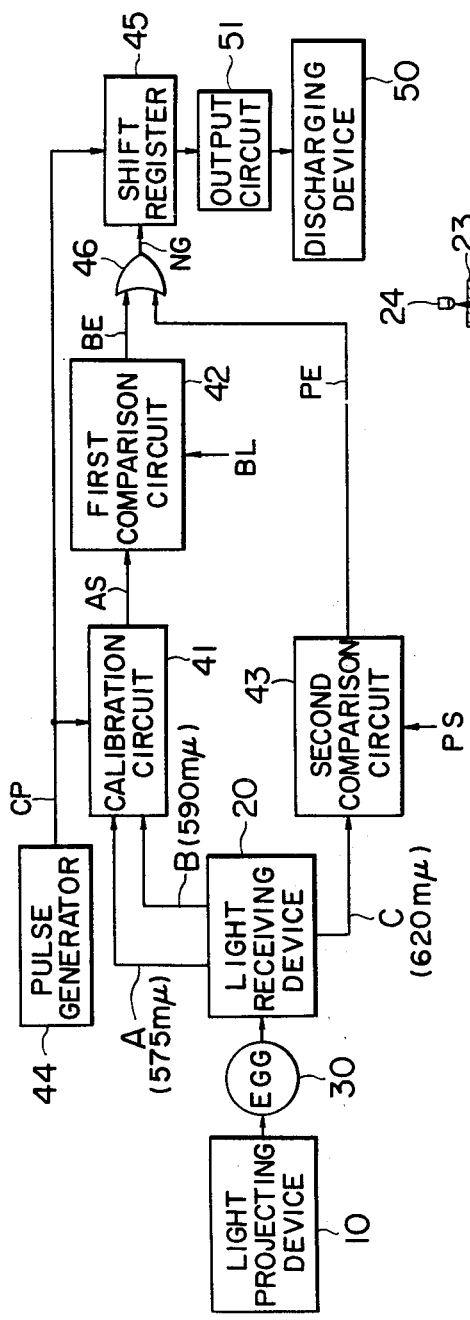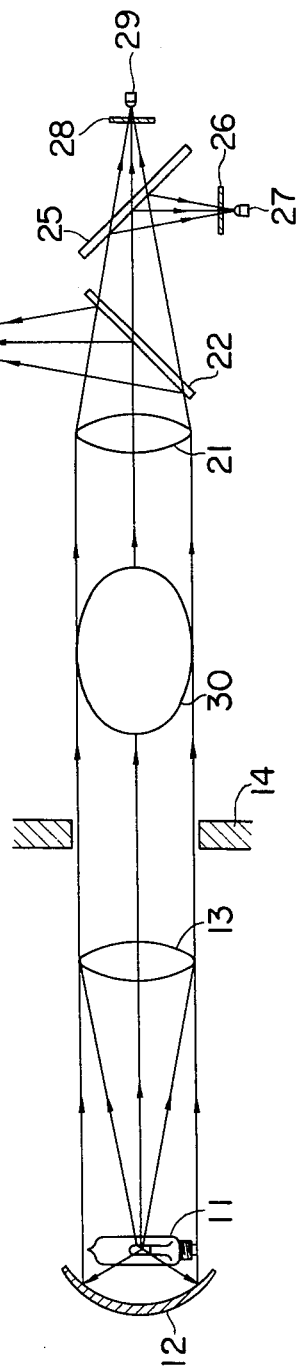

EGG INSPECTING APPARATUS

BACKGROUND OF THE INVENTION

This invention relates to egg inspecting apparatus, and more particularly to apparatus for inspecting quality of eggs without breaking them, or determining whether or not mixtures such as for instance blood are contained therein or deciding whether or not the eggs are turbid eggs, addled eggs, green eggs or moldy egg.

An egg inspecting apparatus has been proposed in which light beams having a wave length of 575 m$\mu$ which is absorbed by the egg blood and a wave length of 600 m$\mu$ which is not absorbed by the egg blood are applied to an egg to be inspected, and the light beam passing through the egg are compared with each other thereby to determined whether or not the egg contains blood. In this case, as the intensity of the light beam passing through the egg depends greatly on the egg's optical density such as the thickness or color of the egg, it is difficult to determine whether or not the egg contains blood by simply comparing the intensities of the light beams passed through the egg.

In order to overcome this difficulty, a method has been provided in which irrespective of the egg's optical density the light reception level of the light beam of 600 m$\mu$ (which is not absorbed by the egg blood) passed through the egg is maintained unchanged, and it is determined whether the egg contains blood by comparing this light reception signal with the light reception signal of the light beam of 575 m$\mu$ which is absorbed by the egg blood. However, this method also suffers from a drawback that there is a risk of erroneously determining good eggs to be addled eggs or blood-containing eggs.

SUMMARY OF THE INVENTION

Accordingly, it is an object of this invention to eliminate all of the above-described difficulties accompanying a conventional egg inspecting apparatus.

More specifically, an object of the invention is to provide an egg inspecting apparatus which can positively select or determine defective eggs irrespective of egg's optical characteristics such as the thickness or color of eggs, and the effect of egg-shells.

The foregoing object and other objects of the invention have been achieved by the provision of an egg inspecting apparatus which, according to the invention, comprises: a light projecting circuit for projecting light to an egg to be inspected; a light receiving circuit in which light beams passed through the egg are converted into electrical signals in the wave length ranges of 575 m$\mu$, 590 m$\mu$ and 620 m$\mu$ to output light reception signals, respectively; a calibration circuit for calibrating the light reception signal of 575 m$\mu$ on the basis of the light reception signal of 590 m$\mu$ to provide a calibration signal; a first comparison circuit for comparing the calibration signal with a predetermined blood-containing egg level; and a second comparison circuit for comparing the light reception signal of 620 m$\mu$ with a predetermined addled egg level, so that a defective egg signal is obtained from the outputs of the first and second comparison circuit.

The nature, principle and utility of the invention will become more apparent from the following detailed description and the appended claims when read in conjunction with the accompanying drawings, in which like parts are designated by like reference numerals or characters.

BRIEF DESCRIPTION OF THE DRAWINGS

In the accompanying drawings:

FIG. 1 is a graphical representation indicating characteristics of various eggs on which this invention has been developed;

FIG. 2 is a block diagram illustrating one example of an egg inspecting apparatus according to this invention;

FIG. 3 is an explanatory diagram showing a part of the egg inspecting apparatus in detail;

DETAILED DESCRIPTION OF THE INVENTION

Figure 4:
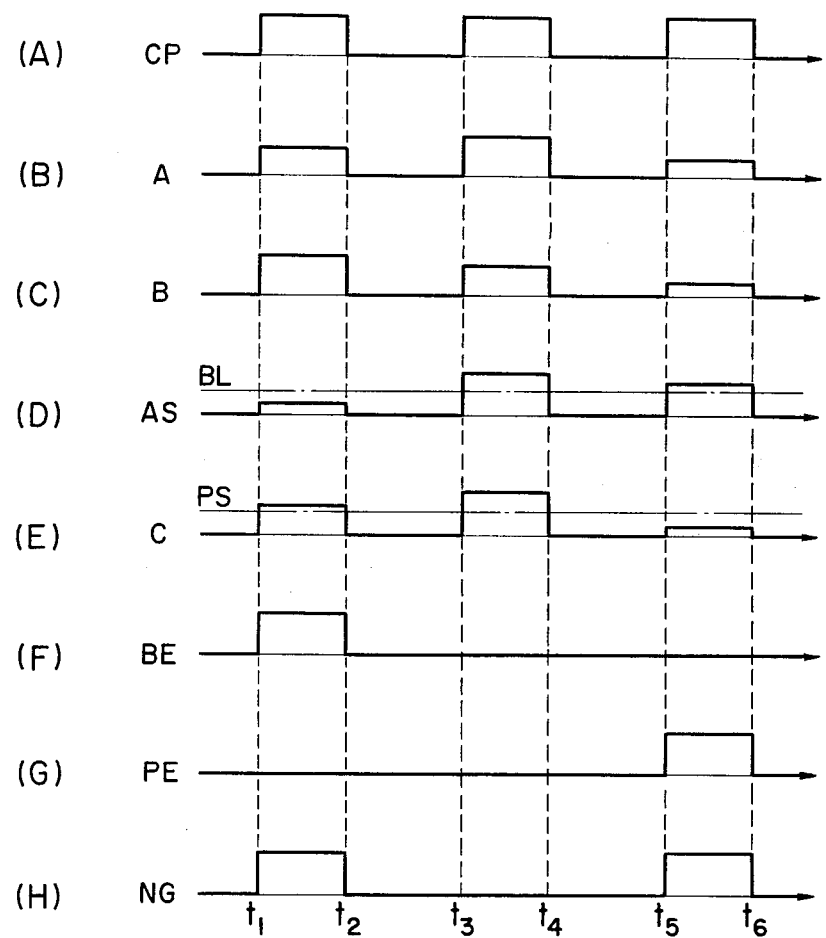
FIG. 4 is a time chart for a description of the operation of the egg inspecting apparatus shown in FIG. 2.

In this invention, judging from the ratios of light beams passed through various eggs, which are measured by a spectrophotometer, as indicated in FIG. 1, optical wave lengths of approximately 575 m$\mu$, 590 m$\mu$ and 620 m$\mu$ are employed to inspect quality of eggs. In FIG. 1, the light transmission characteristic of an egg which is new and has a white egg-shell is indicated by a characteristic curve A; the light transmission characteristic of an egg which is old and has a white egg-shell, by a characteristic curve B; the light transmission characteristic of an addled egg, by a characteristic curve C; the light transmission characteristic of an egg which has a white egg-shell and contains blood, by a characteristic curve D; the light transmission characteristic of an egg which is new and has a dark brown egg-shell, by a characteristic curve E; and the light transmission characteristic of an egg which is new and has a light brown egg-shell by curve F. As is apparent from these characteristic curves, the optical wave lengths of 575 m$\mu$, 590 m$\mu$ and 620 m$\mu$ are suitable for determining whether all the kinds of egg are defective or not.

The selection results of the conventional apparatus, in which comparison is effected with the optical wave lengths of 575 m$\mu$ and 600 m$\mu$, carried out by adding the optical wave length of 600 m$\mu$ to the above-described three optical wave lengths 575 m$\mu$, 590 m$\mu$ and 620 m$\mu$ are as indicated in Table 1 below;

Table 1

| Wave length Characteristic | 575 m$\mu$ | 590 m$\mu$ | 600 m$\mu$ | 620 m$\mu$ | Selection Results of conventional apparatus |
| --- | --- | --- | --- | --- | --- |
| A | 107% | 91% | 87% | 75% | Good eggs |
| B | 49% | 44 | 56 | 45 | Blood-containing eggs |
| C | 25 | 26 | 27 | 28 | Blood-containing eggs and addled eggs |
| D | 33 | 70 | 89 | 85 | Blood-containing eggs |
| E | 12 | 8 | 15 | 41 | Blood-containing eggs and addled eggs |
| F | 88 | 77 | 82 | 99 | Good eggs |

As is apparent from Table 1, the eggs of the characteristic E show the phenomenon of blood-containing eggs because they have dark brown egg-shells which absorb the light of 575 m$\mu$, and are erroneously determined to be addled eggs because a certain quantity of light cannot be obtained in the wave length range of 600 mμ. Furthermore, in the case of eggs containing blood in the yolks, which may be regarded as good eggs, the light absorbing levels are substantially equal in the wave length ranges of 575 mμ and 600 mμ, and accordingly sometimes they are determined to be blood-containing eggs.

Because of the above-described reason, in this invention, the comparison of light absorbing levels in the two wave length ranges of 575 mμ and 600 mμ is not employed, but the comparison of light absorbing levels in the three wave length ranges of 575 mμ, 590 mμ and 620 mμ is employed. Since any egg having a dark brown egg-shell which is liable to be erroneously determined shows a peak light quantity at 620 mμ, when the quantity of light is less than 30% of that as shown in Table 1 in the wave length range of 575 mμ, it is not determined to be an addled egg, because an actually addled egg shows a low light absorbing level in the wave length range of 550 to 630 mμ.

Shown in FIGS. 2 and 3 is a perferred example of an egg inspecting apparatus according to this invention, which comprises a light projecting device 10 for illuminating an egg 30 to be inspected which device 10 is made up of a light source or a halogen lamp 11, a reflecting mirror 12 for providing parallel light beams by reflecting light beams from the light source 11, and a light projecting lens 13 and a slit 14 for dealing with the light, of 10,000 to 20000 Luxes, from the halogen lamp 11 and the reflecting mirror 12 to project, in a predetermined range, light of 10,000–20,000 luxes from the halogen lamp 11 and the reflecting mirror 12. The apparatus further comprises a light receiving device 20 which receives the light passed through the egg 30 and subjects it to photo-electrical conversion at optical wave lengths 575 mμ, 590 mμ and 620 mμ to provide light reception signals A, B and C. The light receiving device 20 comprises a light receiving lens for focusing the transmitted light beams, a photo-transistor 24 for receiving the focused light beams separated by a half mirror 22 through an interference filter 23 having a wave length of 620 mμ (6200 Å) to subject them to photo-electrical conversion, a photo-transistor 27 for receiving the focused light beams separated by a half mirror 25 through an interference filter 26 having a wave length of 575 mμ (5750 Å) to subject them to photo-electrical conversion, and a photo-transistor 29 for receiving the focused light beams passed through the half mirrors 22 and 25 through an interference filter 28 having a wave length of 590 mμ (5900 Å) to subject them to photo-electrical conversion. The apparatus further comprises a calibration circuit 41, a first comparison circuit 42, a second comparison circuit 43, a pulse generator 44, a shift register 45, and a discharging device 50. In the calibration circuit 41, the light reception signal A of 575 mμ is calibrated on the basis of the light reception signal B of 590 mμ. In the first comparison circuit 42, a calibration signal AS from the calibration circuit 41 is compared with a predetermined blood-containing egg level BL and when the calibration signal AS is lower than the blood-containing egg level BL, a blood-containing egg signal BE is outputted. In the second comparison circuit 43, the light receiving signal C of 620 mμ from the light receiving device 20 is compared with a predetermined addled-egg level PS and when the light receiving signal C is lower than the addled-egg level PS, an addled-egg signal PE is outputted. The pulse generator 44 generates clock pulses CP for inspecting eggs with predetermined timing. In the shift register 45, the blood-containing egg signal BE of the addled-egg signal PE is received, as a defective-egg signal, through an OR circuit 46, and it is outputted in a predetermined period of time in synchronization with the clock pulse CP. The discharging device 50 is operated by an output circuit 51 in response to a defective egg discharging signal outputted by the shift register 45, to discharge defective eggs.

In operation, the pulse generator 44 produces the clock pulse CP with a period as indicated in the part (A) of FIG. 4, and eggs to be inspected are successively delivered to a predetermined position in synchronization with the clock pulse CP, where the egg is illuminated by the light from the light projecting device 10. The light beams passed through the egg are applied to the light receiving device 20, where they are separated into the light beams of 575 mμ, 590 mμ and 620 mμ by means of the above-described half mirrors 22 and 25 and the interference filters 23, 26 and 28 and are converted into electrical signals, that is, the light reception signals A, B and C by the transistors 24, 27 and 29 in correspondence to the quantities of light received thereby as indicated in the parts (B), (C) and (E) of FIG. 4. The light reception signals A and B are applied to the calibration circuit 41, while the light reception signal C is applied to the comparison circuit 43.

It is assumed that the ratio of the light reception signal B with respect to one (1) is expressed by 1/B, and this ratio is a signal X for calibrating the light reception signal A. If the light reception signal B is multiplied by the calibrating signal X, then the value of the light reception signal A with the light reception signal B as one (1) can be obtained. If this signal is subtracted from one (1), then it can be seen in what ratio the light reception signal A is greater than or smaller than the light reception signal B. The signal thus obtained will be referred to as the calibration signal AS. In other words, in the calibration circuit 41 the calculation of the following equation (1) is performed to output the calibration signal AS.

$$AS = 1 - AX = 1 - A/B = (B - A)/B \quad (1)$$

The calibration signal is provided in synchronization with the clock pulse CP generated by the pulse generator 44, and is applied to the comparison circuit 42 where it is compared with the blood-containing egg level BL. On the other hand, the light reception signal C is applied to the comparison circuit 43 where it is compared with the addled-egg level PS. When the calibration signal AS becomes lower than the blood-containing egg level BL for the period of time of from the time instant $t_1$ to the time instant $t_2$ as indicated in FIG. 4, the blood-containing egg signal BE is outputted. Furthermore, when the light reception signal C becomes lower than the addled egg level PS for the period of time $t_5 - t_6$, the addled egg signal PE is outputted. The blood-containing signal BE or the addled egg signal PE thus outputted is applied, as the defective egg signal NG, to the shift register 45 through the OR circuit 46. The defective egg signal NG thus stored in the shift register 45 is outputted in synchronization with the clock pulse CP in a predetermined period of time, that is, when the defective egg reaches the defective egg discharging position, so that the defective egg is discharged by the discharging device 50 operated by the output circuit 51. Thus, only the defective eggs can be discharged.

Figure 5:
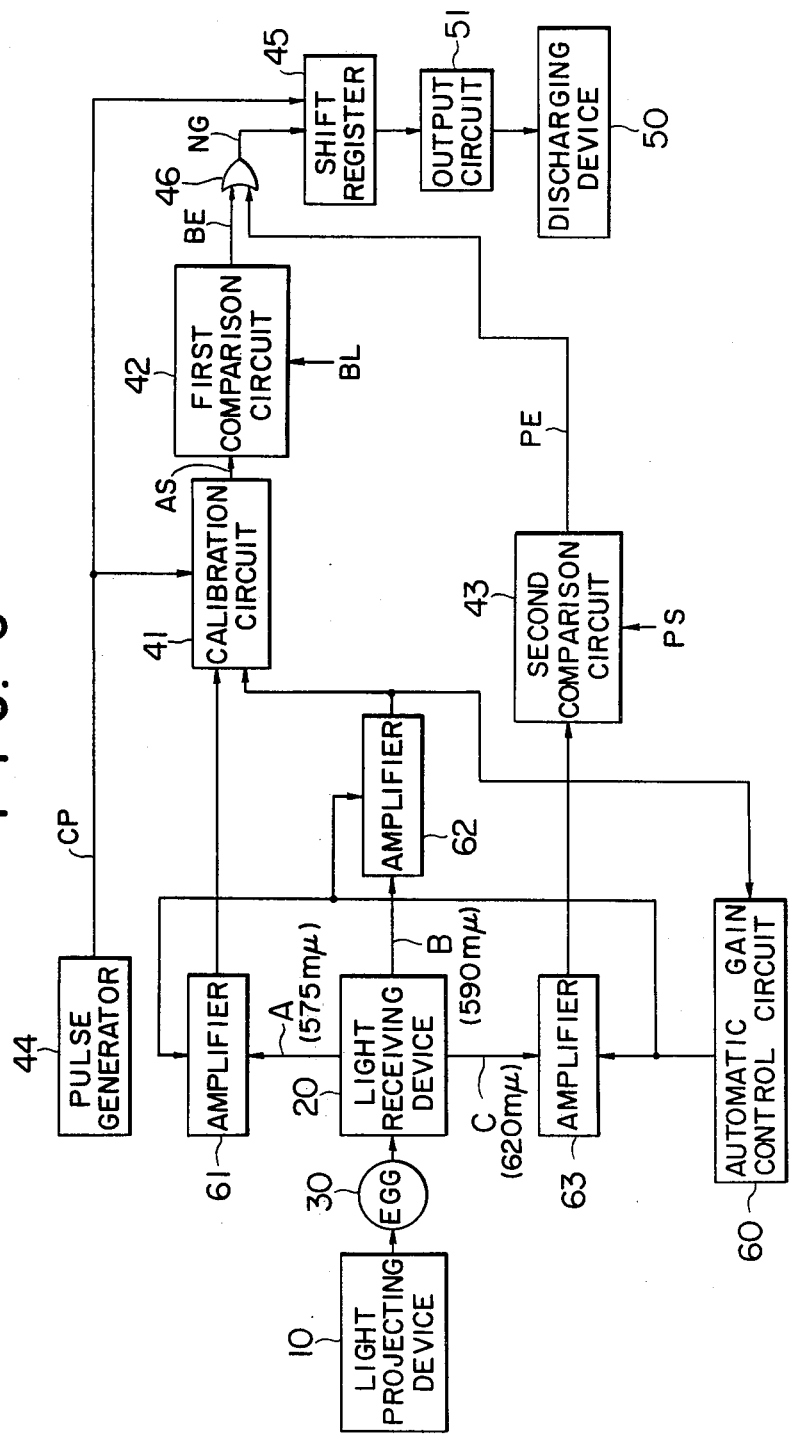
FIG. 5 is a block diagram showing another example of the egg inspecting apparatus according to the invention.

Shown in FIG. 5 is another example of the egg inspecting apparatus according to the invention. As is apparent from comparison of FIG. 5 with FIG. 2, this example is obtained by adding several circuits to those shown in FIG. 2. More specifically, the egg inspecting apparatus is additionally provided with an automatic gain control circuit 60, an amplifier 61 of the 575 mμ light reception system, an amplifier 62 of the 590 mμ light reception system, and an amplifier 63 of the 620 mμ light reception system. The frequency of an accumulation effect light reception oscillator is controlled by the automatic gain control voltage on the basis of the output of the amplifier 62, so as to automatic-gain-control the light reception sensitivities of the amplifiers 61, 62 and 63, thereby to increase the dynamic ranges of these amplifiers 61, 62 and 63 with respect to the quantity of incident light.

It should be noted that green eggs and moldy eggs can be rejected by the use of the above-described egg inspection apparatus.

As is apparent from the above-description, in this invention, the light reception signal of 575 mμ is calibrated on the basis of the light reception signal of 590 mμ and is compared with the predetermined blood-containing egg level to select blood-containing eggs, and the light reception signal of 620 mμ is compared with the predetermined addled egg level to select addled eggs. Accordingly, with the egg inspecting apparatus according to this invention, it is possible to correctly decide whether or not eggs are defective, and the decision is not affected by the thickness or color of eggshells. Furthermore, even brown eggs can be inspected without increasing the sensitivity of the apparatus, that is, in this case it is unnecessary to complement the sensitivity.

In the apparatus described above, the defective egg signal is once stored in the shift register; however, the egg inspecting apparatus may be so designed that the defective egg is discharged directly in response to the defective egg signal. Furthermore, the photo-transistor is employed as the photo-electrical converting element in the above-described apparatus; however, it may be replaced by other photo-electrical converting elements.

What is claimed is:

1. An egg inspecting apparatus comprising: a light projecting means for projecting light to an egg to be inspected; a light receiving means in which light beams passed through said egg are converted into electrical signals in the wave length ranges of 575 mμ, 590 mμ and 620 mμ to output light reception signals, respectively; a calibration means for calibrating said light reception signal of 575 mμ on the basis of said light reception signal of 590 mμ to provide a calibration signal; a first comparison means for comparing said calibration signal with a predetermined blood containing egg level; and a second comparison means for comparing said light reception signal of 620 mμ with a predetermined addled egg level, thereby to obtain a defective egg signal from outputs of said first and second comparison means.

2. An egg inspecting apparatus defined in claim 1 wherein a light projecting means comprise a halogen lamp, a reflecting mirror for providing parallel light beams and a light projecting lens, and a light receiving means comprise a light receiving lens for focusing the transmitted light beams, a photo-transistor (24) for receiving the focused light beams separated by a half mirror (22) through an interference filter, a photo-transistor (27) for receiving the focused light beams separated by a half mirror (25) through an interference filter (26), and a photo-transistor (29) for receiving the focussed light beams passed through to half mirrors (22) and (25) through an interference filter (28).

* * * * *